US00PP09067P

United States Patent [19]

Carmi

[11] Patent Number: Plant 9,067

[45] Date of Patent: Feb. 28, 1995

[54] FERN PLANT NAMED ORLANDO

[75] Inventor: P. J. Carmi, Apopka, Fla.

[73] Assignee: Milestone Agriculture Inc., Apopka, Fla.

[21] Appl. No.: 270,780

[22] Filed: Jul. 5, 1994

[51] Int. Cl.[6] ..... A01H 5/00

[52] U.S. Cl. ..... Plt./88.3

[58] Field of Search ..... Plt. 88.3

*Primary Examiner*—James R. Feyrer

[57] ABSTRACT

A distinct cultivar of Fern plant named Orlando, characterized by its mature pinnae that are dark green in color; pinnae that are curved inward towards the midvein and strongly undulated from base to tip giving a wavy, not flat, appearance; overlapping pinnae arrangement; numerous pinnae and fronds that form a dense plant canopy; symmetrical and weeping plant shape that is appropriate for hanging basket containers; arching to pendent fronds that cover the container; significant frond strength; and rapid growth rate.

1 Drawing Sheet

The present invention relates to a new and distinctive cultivar of Fern plant, botanically known as *Nephrolepis exaltata,* and hereinafter referred to by the cultivar name Orlando.

The new cultivar was discovered by me at Milestone Agriculture, Inc., Apopka, Fla., as a naturally occurring sport or mutation of the nonpatented *Nephrolepis exaltata* cultivar Compacta.

Asexual reproduction of the new cultivar by tissue culture propagation and by divisions taken at Milestone Agriculture, Inc., Apopka, Fla., has shown that the unique features of this new Fern are firmly fixed and retained through successive generations of asexual reproduction.

The cultivar Orlando has not been observed under all possible environmental conditions. The phenotype may vary significantly with variations in environment such as temperature and light intensity. The following observations, measurements and comparisons describe plants grown in Apopka, Fla., under conditions which closely approximate those generally used in commercial practice.

The following traits have been repeatedly observed and are determined to be the unique characteristics of Orlando. These characteristics in combination distinguish Orlando as a new and distinct cultivar:

1. Pinnae that are dark green when mature.
2. Pinnae that are curved inward towards the midvein and strongly undulated from base to tip giving a wavy, not flat, appearance.
3. Pinnae thatr are overlapping in their arrangement.
4. Numerous pinnae and fronds that form a dense plant canopy.
5. Symmetrical and weeping plant shape that is appropriate for hanging basket containers.
6. Arching to pendent fronds that cover the container.
7. Fronds that have significant frond strength.
8. Growth rate that is rapid.

Orlando is most similar to its parent cultivar, the nonpatented *Nephrolepis exaltata* cultivar Compacts, in its similar plant shape and vigor. Orlando differs from Compacta in the following characteristics:

1. Plants of Orlando are most compact in plant habit than plants of Compacta. Compacta plants are wider than plants of Orlando due to the longer frond and rachis lengths of Compacta compared to Orlando plants.

2. Fronds of plants of Orlando are narrower than fronds of plants of Compacta.
3. Plants of Orlando have more pinnae per frond compared to plants of Compacta.
4. Pinnae on plants of Orlando are shorter and narrower than pinnae on plants of Compacta.
5. Pinnae tip shape on plants of Orlando is acute compared to rounded pinnae tip shape on plants of Compacta.
6. Pinnae base shape on plants of Orlando is auriculate compared to truncate pinnae base shape on plants of Compacta.
7. Pinnae of plants of Orlando are curved inward towards the midvein and strongly undulated from base to tip giving a wavy, not flat, appearance. Pinnae of plants of Compacta are slightly curved inward towards the midvein or are flat.
8. Pinnae of plants of Orlando are dark green and shiny compared to medium green and dull appearance of pinnae of plants of Compacta.
10. Pinnae arrangement is different, that is, pinnae of plants of Orlando overlap, pinnae of plants of Compacta do not overlap.

A detailed comparison of Orlando and Compacta plants appears in Chart A at the end of the specification.

The accompanying colored photographs illustrate the overall appearance of the new cultivar, showing the colors as true as it is reasonably possible to obtain in colored reproductions of this type. The photograph at the top of the sheet comprises a top perspective view of a typical potted plant of Orlando. The photograph at the bottom of the sheet is a comparison view of fronds of Orlando (top) and Compacta (bottom). In this comparison photograph, the depicted colors are not precise, but the differences in frond and rachis length, quantity of pinnae per frond, pinnae length, pinnae width, pinnae aspect, and pinnae arrangement are visible.

In the following description, color references are made to The Royal Horticultural Society Colour Chart except where general terms of ordinary dictionary significance are used. Measurements and numerical values represent averages for six typical plants.

Botanical classification: *Nephrolepis exaltata* cultivar Orlando.

Parentage: Naturally occurring sport or mutation of the nonpatented *Nephrolepis exaltata* cultivar Compacta.

Propagation: By tissue culture and divisions

Rooting habit: Fibrous, branching and aggressive. Tissue culture plantlets develop roots within 7 days under warm (80° F.) conditions.

PLANT DESCRIPTION

A. Plant shape: Symmetrical and weeping in shape. Maintains compact size over time. Fronds of mature plants cover the entire container. Appropriate for hanging basket containers.

B. Growth habit: Arching to pendent.

C. Plant height: 35.5 cm from soil line to top of plant plane.

D. Plant width: 75 cm in diameter.

E. Plant vigor: Moderate.

F. Frond description:

1. *Leaf arrangement.*—One-pinnate.
2. *Frond length.*—39 cm.
3. *Frond width.*—6 cm.
4. *Rachis length.*—28 cm.
5. *Quantity of fronds.*—Numerous.

G. Pinnae description:

1. *Pinnae length.*—32 mm.
2. *Pinnae width.*—8.5 mm.
3. *Quantity of pinnae.*—137 per frond.
4. *Margin.*—Very finely crenate.
5. *Number of lobes.*—Numerous.
6. *Pinnae tip.*—Acute.
7. *Pinnae base.*—Auriculate.
8. *Pinnae aspect.*—Curved inward to midvein, strongly undulated from pinnae base to tip giving a wavy, not flat, appearance.
9. *Pinnae arrangement.*—Overlapping.
10. *Pinnae attachment.*—Sessile.
11. *Pinnae texture.*—Shiny, smooth.
12. *Pinnae color.*—a. Immature, top side: 144A. b. Immature, under side: 144A. C. Mature, top side: 137A. d. Mature, under side: 137C.
13. *Venation pattern.*—Pinnate.

Disease resistance: No resistance nor susceptibility to pathogens has been noted.

Spore formation: The new cultivar has not been observed to form spores.

CHART A

| CHARACTERISTIC | COMPACTA | ORLANDO |
|---|---|---|
| PLANT SHAPE | Weeping Symmetrical | Weeping Symmetrical |
| GROWTH HABIT | Upright and arching | Arching to pendent |
| PLANT HEIGHT | 38 cm | 35.5 cm |
| PLANT WIDTH | 88 cm | 75 cm |
| VIGOR | Moderate | Moderate |
| SUITABLE CONTAINER(S) | Hanging baskets | Hanging baskets |
| LEAF ARRANGEMENT | 1-pinnate | 1-pinnate |
| FROND LENGTH | 53 cm | 39 cm |
| FROND WIDTH | 8.5 cm | 6 cm |
| RACHIS LENGTH | 49.5 | 28 |
| QUANTITY OF FRONDS | Many, dense form | Many, dense form |
| QUANTITY OF PINNAE | 108 | 137 |
| PINNAE LENGTH | 41 | 32 |
| PINNAE WIDTH | 12 | 8.5 |
| PINNAE MARGIN | Very finely crenate | Very finely crenate |
| NUMBER OF LOBES | Numerous | Numerous |
| PINNAE TIP | Rounded | Acute |
| PINNAE BASE | Truncate | Auriculate |
| PINNAE ASPECT | Slightly curved inward to midvein to flat | Curved inward to midvein, strongly undulated from base to tip giving a wavy, not flat, appearance |
| PINNAE ATTACHMENT | Sessile | Sessile |
| PINNAE TEXTURE | Dull, smooth | Shiny, smooth |
| PINNAE COLOR, IMMATURE, TOP SIDE | 144A | 144A |
| PINNAE COLOR, IMMATURE, UNDER SIDE | 144A | 144A |
| PINNAE COLOR, MATURE, TOP SIDE | 146A | 137A |
| PINNAE COLOR, MATURE, UNDER SIDE | 137C | 137C |
| PINNAE ARRANGEMENT | Not overlapping | Overlapping |
| VENATION PATTERN | Pinnate | Pinnate |

I claim:

1. A new and distinct cultivar of Fern plant named Orlando, as illustrated and described.

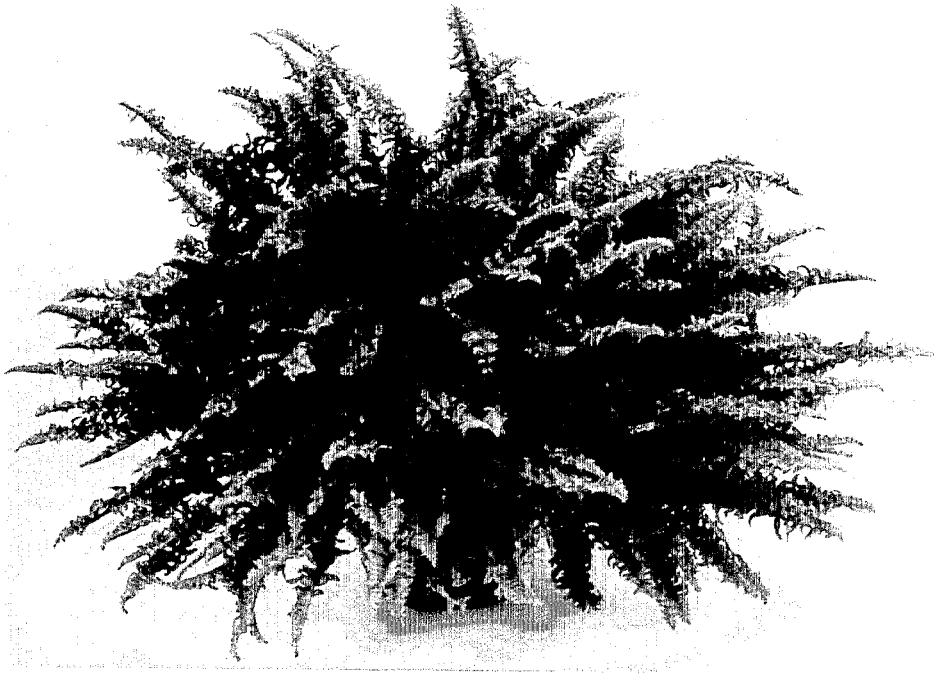
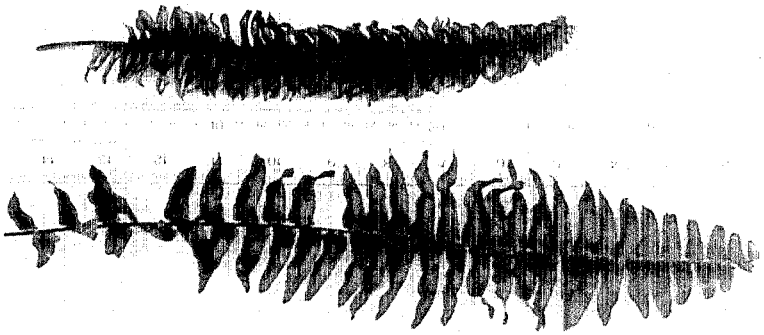

* * * * *